(12) United States Patent
Lipshutz (10) Patent No.: US 12,234,474 B2
(45) Date of Patent: Feb. 25, 2025

(54) METHOD TO PREVENT THE MYELIN ABNORMALITES ASSOCIATED WITH ARGINASE DEFICIENCY

(71) Applicant: The Regents of the University of California, Oakland, CA (US)

(72) Inventor: Gerald Lipshutz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 787 days.

(21) Appl. No.: 17/606,583

(22) PCT Filed: May 7, 2020

(86) PCT No.: PCT/US2020/031891
§ 371 (c)(1),
(2) Date: Oct. 26, 2021

(87) PCT Pub. No.: WO2020/227542
PCT Pub. Date: Nov. 12, 2020

(65) Prior Publication Data
US 2022/0220503 A1    Jul. 14, 2022

Related U.S. Application Data

(60) Provisional application No. 62/844,964, filed on May 8, 2019.

(51) Int. Cl.
*C12N 15/86* (2006.01)
*A61K 31/7088* (2006.01)
*A61K 48/00* (2006.01)

(52) U.S. Cl.
CPC .......... *C12N 15/86* (2013.01); *A61K 31/7088* (2013.01); *A61K 48/00* (2013.01); *C12N 2750/14143* (2013.01); *C12N 2830/50* (2013.01)

(58) Field of Classification Search
CPC ..... C12N 15/86; A61K 31/7088; A61K 48/00
See application file for complete search history.

(56) References Cited

U.S. PATENT DOCUMENTS 7,319,011 B2 *   1/2008   Riggins ............ G01N 33/57407
                                                435/7.1
8,999,380 B2 *   4/2015   Bancel .................. C12N 15/87
                                                 530/358

(Continued)

FOREIGN PATENT DOCUMENTS

WO        1998024473        6/1998

OTHER PUBLICATIONS

PCT International Search Report & Written Opinion dated Oct. 9, 2020 for PCT Application No. PCT/US20/31891.

*Primary Examiner* — Arthur S Leonard
*Assistant Examiner* — Keenan A Bates
(74) *Attorney, Agent, or Firm* — Gates & Cooper LLP (57) ABSTRACT

The invention disclosed herein provides methods and materials useful in gene therapy regimens designed to inhibit myelination abnormalities that occur in the urea cycle disorder arginase deficiency. The underlying cause of the progressive neurological dysfunction that occurs in this disorder has been previously unknown and conventional therapies, at best, only slow the onset of neurological dysfunction. This neurological dysfunction results at least in part from the dysmyelination that occurs in the central nervous system due to the lack of adequate hepatic expression of arginase 1. We have discovered an origin of this neurological dysfunction and, using this information, designed materials and associated methods of gene therapy.

(Continued)

Human Codon-Optimized Arginase 1 Expressing Adeno-Associated Viral (AAV) Vector. The single strand of DNA is packaged in an AAV serotype RH10 capsid and serotype 2 inverted terminal repeats (ITRs). The expression of arginase 1 is controlled by a liver-specific promoter to limit expression to hepatocytes. Gene expression can be increased by the use of a 5' intron.

The methods and materials disclosed herein can inhibit and essentially prevent neurological dysfunction in a murine model of arginase deficiency.

20 Claims, 2 Drawing Sheets

Specification includes a Sequence Listing.

(56) References Cited

U.S. PATENT DOCUMENTS

2010/0249208 A1* 9/2010 Hecker ................... A61P 25/00
 435/375
2013/0259924 A1 10/2013 Bancel et al.

* cited by examiner

Figure 1:
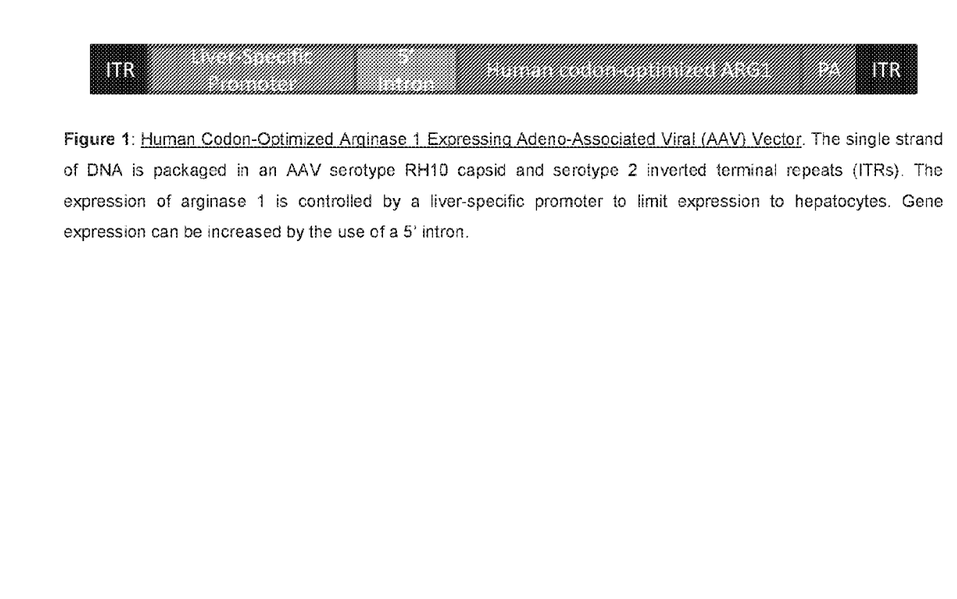
FIG. 1 is a cartoon schematic showing an illustrative Human Codon-Optimized Arginase 1 Expressing Adeno-Associated Viral (AAV) Vector. The single strand of DNA is packaged in an AAV capsid and serotype 2 inverted terminal repeats (ITRs). The expression of arginase I is controlled by a liver-specific promoter to limit expression to hepatocytes. Gene expression can be increased by the use of a 5' intron.

Figure 1: Human Codon-Optimized Arginase 1 Expressing Adeno-Associated Viral (AAV) Vector. The single strand of DNA is packaged in an AAV serotype RH10 capsid and serotype 2 inverted terminal repeats (ITRs). The expression of arginase 1 is controlled by a liver-specific promoter to limit expression to hepatocytes. Gene expression can be increased by the use of a 5' intron.

Figure 2:
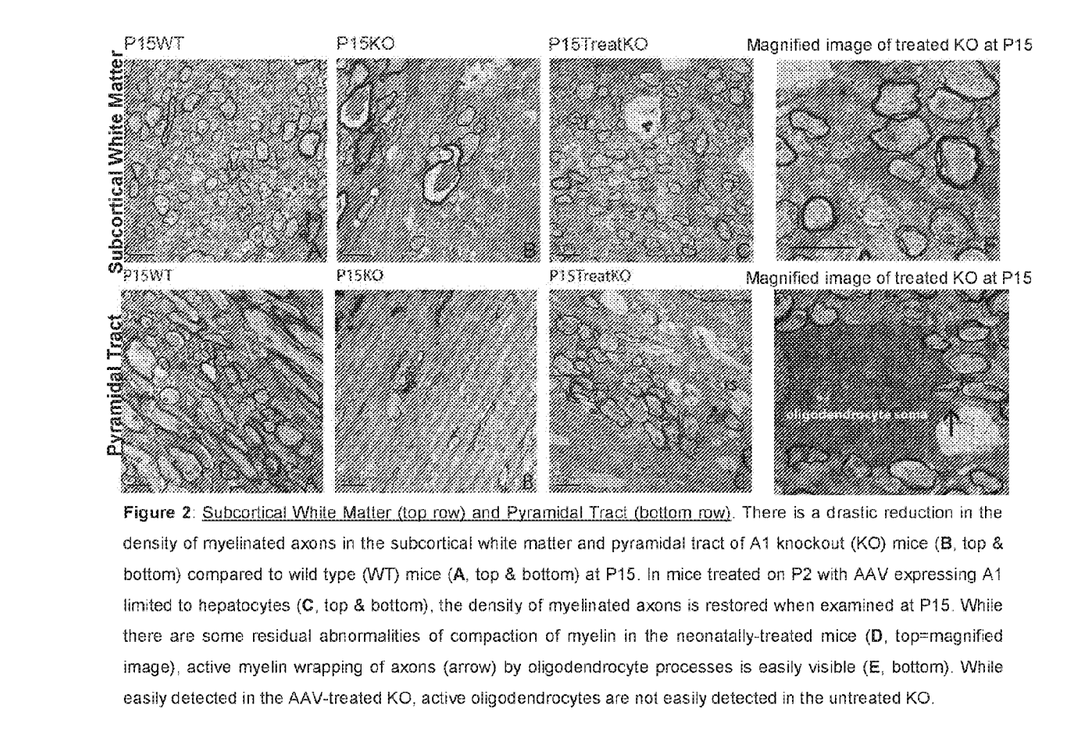
FIG. 2 provides graphs of data showing Subcortical White Matter (top row) and Pyramidal Tract (bottom row). There is a drastic reduction in the density of myelinated axons in the subcortical white matter and pyramidal tract of A1 knockout (KO) mice (B, top & bottom) compared to wild type (WT) mice (A, top & bottom) at P15. In mice treated on P2 with AAV expressing A1 limited to hepatocytes (C, top & bottom), the density of myelinated axons is restored when examined at P15. While there are some residual abnormalities of compaction of myelin in the neonatally-treated mice (D, top=magnified image), active myelin wrapping of axons (arrow) by oligodendrocyte processes is easily visible (E, bottom), While easily detected in the AAV-treated KO, active oligodendrocytes are not easily detected in the untreated KO.

Figure 2. Subcortical White Matter (top row) and Pyramidal Tract (bottom row). There is a drastic reduction in the density of myelinated axons in the subcortical white matter and pyramidal tract of A1 knockout (KO) mice (B, top & bottom) compared to wild type (WT) mice (A, top & bottom) at P15. In mice treated on P2 with AAV expressing A1 limited to hepatocytes (C, top & bottom), the density of myelinated axons is restored when examined at P15. While there are some residual abnormalities of compaction of myelin in the neonatally-treated mice (D, top=magnified image), active myelin wrapping of axons (arrow) by oligodendrocyte processes is easily visible (E, bottom). While easily detected in the AAV-treated KO, active oligodendrocytes are not easily detected in the untreated KO.

SEQUENCE LISTING

<160> NUMBER OF SEQ ID NOS: 9

<210> SEQ ID NO 1
<211> LENGTH: 322
<212> TYPE: PRT
<213> ORGANISM: Homo sapiens

<400> SEQUENCE: 1

```
Met Ser Ala Lys Ser Arg Thr Ile Gly Ile Gly Ala Pro Phe Ser
1               5                   10                  15

Lys Gly Gln Pro Arg Gly Gly Val Glu Glu Gly Pro Thr Val Leu Arg
            20                  25                  30

Lys Ala Gly Leu Leu Glu Lys Leu Lys Glu Gln Glu Cys Asp Val Lys
        35                  40                  45

Asp Tyr Gly Asp Leu Pro Phe Ala Asp Ile Pro Asn Asp Ser Pro Phe
    50                  55                  60

Gln Ile Val Lys Asn Pro Arg Ser Val Gly Lys Ala Ser Glu Gln Leu
65                  70                  75                  80

Ala Gly Lys Val Ala Glu Val Lys Lys Asn Gly Arg Ile Ser Leu Val
            85                  90                  95
```

Leu Gly Gly Asp His Ser Leu Ala Ile Gly Ser Ile Ser Gly His Ala
            100                 105                 110

Arg Val His Pro Asp Leu Gly Val Ile Trp Val Asp Ala His Thr Asp
        115                 120                 125

Ile Asn Thr Pro Leu Thr Thr Thr Ser Gly Asn Leu His Gly Gln Pro
    130                 135                 140

Val Ser Phe Leu Leu Lys Glu Leu Lys Gly Lys Ile Pro Asp Val Pro
145                 150                 155                 160

Gly Phe Ser Trp Val Thr Pro Cys Ile Ser Ala Lys Asp Ile Val Tyr
                165                 170                 175

Ile Gly Leu Arg Asp Val Asp Pro Gly Glu His Tyr Ile Leu Lys Thr
            180                 185                 190

Leu Gly Ile Lys Tyr Phe Ser Met Thr Glu Val Asp Arg Leu Gly Ile
        195                 200                 205

Gly Lys Val Met Glu Glu Thr Leu Ser Tyr Leu Leu Gly Arg Lys Lys
    210                 215                 220

Arg Pro Ile His Leu Ser Phe Asp Val Asp Gly Leu Asp Pro Ser Phe
225                 230                 235                 240

Thr Pro Ala Thr Gly Thr Pro Val Val Gly Gly Leu Thr Tyr Arg Glu
                245                 250                 255

Gly Leu Tyr Ile Thr Glu Glu Ile Tyr Lys Thr Gly Leu Leu Ser Gly
            260                 265                 270

Leu Asp Ile Met Glu Val Asn Pro Ser Leu Gly Lys Thr Pro Glu Glu
        275                 280                 285

Val Thr Arg Thr Val Asn Thr Ala Val Ala Ile Thr Leu Ala Cys Phe
    290                 295                 300

Gly Leu Ala Arg Glu Gly Asn His Lys Pro Ile Asp Tyr Leu Asn Pro
305                 310                 315                 320

Pro Lys

<210> SEQ ID NO 2
<211> LENGTH: 969
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgagcgcaa agtctcgaac aattggcata attggtgctc cgttcagcaa aggtcagcca      60
aggggcggcg tggaggaagg acccacagtg ctgagaaaag ccggcctgct ggagaaactg     120
aaggaacagg aatgtgacgt gaaggactat ggggatctgc cttttgccga tataccgaat     180
gattcaccct tccaaattgt gaaaaatcca agatccgtgg gcaaagcaag tgaacagttg     240
gccgggaagg tggcagaggt taaaaaaaat ggaaggatca gcctcgtact gggtggcgat     300
cactctcttg caattggaag tatttcaggc catgcccgcg ttcatcccga tctcggcgtg     360
atctgggttg atgctcatac agatatcaat ccccctctga cgacaacatc tgggaacctg     420
catggacaac tgtatcatt tctgttgaag gaactgaaag gcaaaatacc cgacgtgcct     480
ggattttcat gggtgacccc ctgcatctct gctaaagaca tagtttacat aggtctgcgc     540
gacgttgatc ctggagaaca ttacattctc aagacactcg gaattaaata tttcagtatg     600
acagaagtgg accgctcgg gattggcaaa gtaatggagg agactctttc atacctgctg     660
ggacgcaaaa aacgaccgat tcacctcagc tttgacgtcg atggacttga cccatctttt     720

```
acaccagcta ctggaacacc agttgtagga ggtcttactt accgcgaagg tctgtatata    780
actgaagaga tttataagac tggacttctc agtggacttg atattatgga agtgaaccct    840
agcctgggaa aaacaccaga agaagtcaca cgcaccgtca ataccgccgt ggctatcacc    900
ctggcttgtt tcggcttggc acgcgaaggg aatcataaac ctattgacta cctgaatccc    960
ccaaagtaa                                                             969
```

<210> SEQ ID NO 3
<211> LENGTH: 354
<212> TYPE: PRT
<213> ORGANISM: Homo sapiens

<400> SEQUENCE: 3

```
Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
        35                  40                  45

Ile Arg Glu Ala Gly Leu Met Lys Arg Leu Ser Ser Leu Gly Cys His
    50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
        115                 120                 125

Gly His Ala Arg His Cys Pro Asp Leu Cys Val Val Trp Val Asp Ala
    130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Pro Glu His Phe Ile
        195                 200                 205

Leu Lys Asn Tyr Asp Ile Gln Tyr Phe Ser Met Arg Asp Ile Asp Arg
    210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
        275                 280                 285

Leu Ser Ala Leu Asp Leu Val Glu Val Asn Pro Gln Leu Ala Thr Ser
    290                 295                 300

Glu Glu Glu Ala Lys Thr Thr Ala Asn Leu Ala Val Asp Val Ile Ala
305                 310                 315                 320
```

Ser Ser Phe Gly Gln Thr Arg Glu Gly Gly His Ile Val Tyr Asp Gln
            325                 330                 335

Leu Pro Thr Pro Ser Ser Pro Asp Glu Ser Glu Asn Gln Ala Arg Val
            340                 345                 350

Arg Ile

<210> SEQ ID NO 4
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| atggtccaca | gcgttgccgt | cattggtgca | ccattctcac | aaggccagaa | aagaaagggc | 60 |
| gtggaacatg | gccctgctgc | aataagagag | gccggactga | tgaaaagact | gtcttcccct | 120 |
| ggctgccatc | ttaaagactt | cggtgatctc | agcttcactc | ctgttccgaa | agacgacctc | 180 |
| tacaacaacc | ttatcgtaaa | tcctagatcc | gtaggtcttg | ctaatcaaga | attggctgag | 240 |
| gtggtttccc | gagcagtttc | cgacggatat | agctgcgtga | ccctcggcgg | tgaccattcc | 300 |
| ctggcaattg | gtacaattag | cggacacgca | agacattgcc | ctgatctctg | tgtggtatgg | 360 |
| gttgacgcgc | atgctgatat | aaatacgcct | ctcaccacct | cctctggcaa | tctgcacgga | 420 |
| cagcccgtgt | cctttctcct | ccgcgaactc | aggacaagg  | tgccacaact | ccccgggttc | 480 |
| tcttggatca | gccctgcat  | ttcatccgct | agtatagtgt | acatcggcct | tagagacgtc | 540 |
| gacccaccag | agcatttcat | cctcaaaaat | tatgacattc | agtactttag | tatgcgcgac | 600 |
| attgacaggc | tgggtattca | gaaagtgatg | gaaaggacgt | tcgacctgtt | gatcggcaaa | 660 |
| agacagagac | caattcacct | cagctttgat | attgatgcat | tcgatcctac | gctcgctccg | 720 |
| gcaacaggga | caccagtggt | aggaggcctg | acttatagag | aaggtatgta | catagccgaa | 780 |
| gaaatacaca | acactggact | gcttagcgcg | cttgaccttg | ttgaagttaa | tccccagctc | 840 |
| gccacgtccg | aggaagaggc | caagaccaca | gctaatctcg | cagttgatgt | aatagcatct | 900 |
| agttttggac | agacccgaga | aggagggcac | atcgtgtatg | accagctccc | tacaccgagt | 960 |
| tcacctgatg | agtcagaaaa | tcaagcccgg | gtccgcattt | ag         |            | 1002 |

<210> SEQ ID NO 5
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct |            |            |            |            |            | 130 |

<210> SEQ ID NO 6
<211> LENGTH: 460
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 6
gggctggaag ctacctttga catcatttcc tctgcgaatg catgtataat ttctacagaa    60
cctattagaa aggatcaccc agcctctgct tttgtacaac tttcccttaa aaaactgcca   120
attccactgc tgtttggccc aatagtgaga acttttttcct gctgcctctt ggtgcttttg   180
cctatggccc ctattctgcc tgctgaagac actcttgcca gcatggactt aaaccccctcc   240 agctctgaca atcctctttc tcttttgttt tacatgaagg gtctggcagc caaagcaatc   300
actcaaagtt caaaccttat cattttttgc tttgttcctc ttggccttgg ttttgtacat   360
cagctttgaa ataccatcc cagggttaat gctggggtta atttataact aagagtgctc   420
tagttttgca atacaggaca tgctataaaa atggaaagat                          460

<210> SEQ ID NO 7
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                      133

<210> SEQ ID NO 8
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gatctttttc cctctgccaa aaattatggg gacatcatga agcccttga gcatctgact    60 tctggctaat aaaggaaatt tattttcatt gcaatagtgt gttggaattt tttgtgtctc   120
tcactcg                                                             127

<210> SEQ ID NO 9
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                          130
```

METHOD TO PREVENT THE MYELIN ABNORMALITES ASSOCIATED WITH ARGINASE DEFICIENCY

CROSS REFERENCE TO RELATED APPLICATIONS

This application claims the benefit under 35 U.S.C. Section 119(e) of commonly-assigned U.S. Provisional Patent Application Ser. No 62/844,964, filed on May 8, 2019 and entitled "A METHOD TO PREVENT THE MYELIN ABNORMALITES ASSOCIATED WITH ARGINASE DEFICIENCY" which application is incorporated by reference herein.

STATEMENT REGARDING FEDERALLY SPONSORED RESEARCH AND DEVELOPMENT

This invention was made with government support under Grant Number NS101682, awarded by the National Institutes of Health. The government has certain rights in the invention.

TECHNICAL FIELD

The invention relates to methods and materials useful in treating arginase deficiency.

BACKGROUND OF THE INVENTION

Arginase deficiency is an inherited metabolic disease in which the body is unable to process arginine. Arginase deficiency belongs to a group of disorders known as urea cycle disorders. These occur when the body's process for removing ammonia is disrupted, which can cause ammonia levels in the blood to rise (hyperammonemia). In most cases, symptoms appear between the ages of one and three years. Symptoms may include feeding problems, vomiting, poor growth, seizures, and stiff muscles with increased reflexes (spasticity). People with arginase deficiency may also have developmental delay, loss of developmental milestones, and intellectual disability.

Arginase deficiency is typically caused by mutations in the ARG1 gene and is inherited in an autosomal recessive manner. Conventional treatments are focused on lowering arginine levels and preventing hyperammonemia. While the elevated levels of ammonia are infrequent, they can be life-threatening. If untreated, developmental problems and seizures can happen.

In view of this, there is a need for new methods and materials useful to address arginase deficiency.

SUMMARY OF THE INVENTION

The invention disclosed herein provides methods and materials useful in gene therapy regimens designed to inhibit myelination abnormalities that occur in the urea cycle disorder arginase deficiency. The underlying cause of the progressive neurological dysfunction that occurs in this disorder has been previously unknown and conventional therapies, at best, only slow the onset of neurological dysfunction. This neurological dysfunction results at least in part from the dysmyelination that occurs in the central nervous system due to the lack of adequate hepatic expression of arginase 1. We have discovered an origin of this neurological dysfunction and, using this information, designed materials and associated methods of gene therapy. The methods and materials disclosed herein can be used to inhibit and essentially prevent neurological dysfunction in a murine model of arginase deficiency.

As disclosed herein, in a mouse model of arginase deficiency, intravenous administration of an adeno-associated viral vector designed to expresses arginase 1 using a liver-specific promoter shortly after birth can prevent dysmyelination, improve compaction of myelin in the central nervous system, and maintain a near normal dendritic arbor of layer V cortical neurons into adulthood. In addition, these mice appear and have behavior that is indistinguishable from control mice not having arginase deficiency. Moreover, publications in this field provide evidence that abnormalities in myelination similarly occur in humans having arginase deficiency (like mice having arginase deficiency). Consequently, this poorly treated disorder in human patients is amenable to treatment using the methods and materials disclosed herein.

Adeno-associated virus (AAV) is a small virus that infects humans which is useful as a vector to deliver genes to treat human genetic disorders. To illustrate the ability of AAVs to treat arginase deficiency, AAVs encoding a human codon optimized arginase 1 gene driven by a liver specific promoter were generated and tested in a mouse model for human arginase deficiency (see, Iyer et al., Mol Cell Biol. 2002 July;22(13):4491-8. PMID: 12052859). Expression of the endogenous gene takes place in the liver and a liver-specific promoter is used in the working embodiment of the invention in order to obtain liver restricted expression. When administered to mice having knocked out endogenous arginase expression, mice from this model demonstrate therapeutic phenomena including density of myelinated axons being restored following the administration of AAVs comprising arginase 1 polynucleotide sequences (which leads to the expression of the ARG1 protein in these mice). As there is no significantly effective therapy for human patients with the ARG1 deficiency disorder, this treatment is useful to address an unmet need for these patients.

The invention disclosed herein has a number of embodiments. For example, embodiments of the invention include methods of making pharmaceutical compositions useful in gene therapy. Such methods typically comprise comprising combining together in an aqueous formulation at least one adeno-associated viral vector comprising a codon optimized nucleotide sequence encoding an arginase 1 (SEQ ID NO: 1) or arginase 2 polypeptide (SEQ ID NO: 3); and a pharmaceutical excipient selected from the group consisting of a preservative, a tonicity adjusting agent, a detergent, a viscosity adjusting agent, a sugar or a pH adjusting agent. Typically in these methods, the components of the pharmaceutical composition are selected so that when the adeno-associated viral vector(s) in the composition infect a human liver cell, arginase 1 (SEQ ID NO: 1) or arginase 2 polypeptide (SEQ ID NO: 3) is expressed. Typically, the adeno-associated viral vector(s) also comprise additional polynucleotide sequences selected to facilitate the expression of the arginase I protein or arginase 2 protein in a target cell population such as one or more polynucleotide sequences comprising a terminal repeat, a promoter (e.g. a tissue specific promoter), an enhancer, a chimeric intron; a polynucleotide sequence comprising a polyA signal and the like.

Other embodiments of the invention include pharmaceutical compositions comprising a at least one adeno-associated viral vector having a polynucleotide sequence comprising a codon optimized polynucleotide sequence encoding an arginase 1 protein (SEQ ID NO: 1) or an arginase 2 protein (SEQ ID NO: 3) in combination with a pharmaceutical excipient selected from the group consisting of a preservative, a tonicity adjusting agent, a detergent, a viscosity adjusting agent, a sugar or a pH adjusting agent. Typically, the adeno-associated viral vector(s) also comprise a terminal repeat, a polynucleotide sequence comprising a promoter, polynucleotide sequence comprising an enhancer, a polynucleotide sequence comprising a chimeric intron; and/or a polynucleotide sequence comprising a polyA signal.

Related embodiments of the invention include using the compositions disclosed herein in gene therapy methods to treat arginase 1 protein or arginase 2 deficiency. Such methods include, for example methods of delivering codon optimized polynucleotides encoding arginase 1 protein or arginase 2 protein into human cells comprising contacting a composition disclosed herein (e.g. a composition comprising a adeno-associated viral vector comprising a codon optimized polynucleotide sequence encoding arginase 1 or arginase 2) with human cells so that adeno-associated vector (s) infect the cells, thereby delivering the polynucleotides into the cells. In certain embodiments of the invention, the cells are in vivo liver cells, for example in vivo liver cells present in an individual diagnosed with arginase deficiency. Related embodiments of the invention include methods of treating a subject diagnosed with an arginase 1 protein or arginase 2 protein deficiency, comprising selecting a subject with an arginase I protein or arginase 2 deficiency and administering to the subject a therapeutically effective amount of a pharmaceutical composition disclosed herein.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

All publications mentioned herein are incorporated herein by reference to disclose and describe aspects, methods and/or materials in connection with the cited publications (e.g. U.S. Patent Application Publication Numbers 20060115869, 20080176259, 20090311719, 20100183704 and 20190017069, and Diez-Femandez C et al. Expert Opin Ther Targets, 2017 Apr.;21(4):391-399, doi: 10.1080/14728222.2017.1294685, Zhang (3 et al. J Clin Lab Anal. 2018 February;32(2), doi: 10.1002/jcla.22241, Choi R et al. Ann Lab Med. 2017 January;37(1):58-62, doi: 10.3343/alm.2017.37.1.58, Naso et al., BioDrugs (2017) 31:317-334, and Srinivasan et al., J Inherit Metab Dis. 2019 Mar. 6, doi: 10.1002/jimd.12067).

Conventional therapies for arginase deficiency involve dietary restrictions. Such therapies are not completely effective in controlling hyperargininemia and in fact are often poorly tolerated by patients. Patients have a progressive neurological deterioration due to (likely) arginine-related metabolites in their bloodstream that cause neuronal dysfunction or effect normal neuronal development. As rare disease gene therapy clinical trials are advancing, there is an opportunity to bring such a gene therapy approach forward for patients afflicted with this disorder.

As noted above, embodiments of the invention include gene therapy methods that utilize adeno-associated virus (AAV). AAV is a non-enveloped virus that can be engineered to deliver DNA to target cells, which has attracted a significant amount of attention in the field, especially in clinical-stage experimental therapeutic strategies. The ability to generate recombinant AAV particles lacking any viral genes and containing DNA sequences of interest for various therapeutic applications has thus far proven to be one of the safest strategies for gene therapies. The review in Naso et al., BioDrugs (2017) 31:317-334 provides an overview of factors considered in the use of AAV as a vector for gene therapy. U.S. Patent Application Publication Numbers 20190017069 20180163227 20180104289 20170362670 20170348435 20170211095 20170304466 and 20170096682 disclose illustrative AAV methods and materials.

The invention disclosed herein has a number of embodiments. Embodiments of the invention include, for example, methods of making a pharmaceutical composition by combining together in an aqueous formulation a polynucleotide comprising SEQ ID NO: 2 or a polynucleotide comprising SEQ ID NO: 4; and a pharmaceutical excipient selected from the group consisting of a preservative, a tonicity adjusting agent, a detergent, a viscosity adjusting agent, a sugar or a adjusting agent. In typical methods of making such pharmaceutical compositions, the polynucleotide comprising SEQ ID NO: 2 or the polynucleotide comprising SEQ ID NO: 4 is disposed in an adeno-associated viral vector such that when the adeno-associated viral vector infects a human liver cell, arginase I protein (SEQ ID NO: 1) or arginase 2 protein (SEQ ID NO: 3) is expressed. In certain embodiments of these methods, the adeno-associated viral vector comprises elements selected to facilitate arginase 1 or arginase 2 polypeptide expression in cells. Optionally for example, the adeno-associated viral vector comprises a polynucleotide comprising a terminal repeat sequence of SEQ ID NO: 5, a polynucleotide comprising a promoter sequence of SEQ ID NO: 6; and a polynucleotide comprising a poly A tail sequence of SEQ ID NO: 8. In some embodiments of the invention, the adeno-associated viral vector comprises a polynucleotide comprising SEQ ID NO: 2. In some embodiments of the invention, the adeno-associated viral vector comprises a polynucleotide comprising SEQ ID NO: 4.

Embodiments of the invention include compositions of matter comprising a polynucleotide comprising SEQ ID NO: 2; or a polynucleotide comprising SEQ ID NO: 4. In certain embodiments, the composition comprises an adeno-associated viral vector that includes such a polynucleotide sequence operatively linked to a promoter. In this context, a wide variety of promoters can be used with embodiments of the invention including constitutive promoters that are expressed in a wide variety of cell types, as well as cell lineage specific promoters such as the thyroxine binding globulin (TBG promoter) which is liver-specific. Certain illustrative promoters are described, for example in Damdindorj, et al. (2014) A Comparative Analysis of Constitutive Promoters Located in Adeno-Associated Viral Vectors. PLoS ONE 9(8): e106472; as well as Pacak et al., (2008) Tissue specific promoters improve specificity of AAV9 mediated transgene expression following intra-vascular gene delivery in neonatal mice, Genet Vaccines Ther. 2008; 6: 13.

Typically the compositions also includes a polynucleotide comprising SEQ ID NO: 2 or a polynucleotide comprising SEQ ID NO: 4; and a polynucleotide sequence comprising a polyA tail signal; as well as a pharmaceutical excipient selected from the group consisting of a preservative, a tonicity adjusting agent, a detergent, a viscosity adjusting agent, a sugar or a pH adjusting agent. In some embodiments, the composition comprises an adeno-associated viral vector encoding the polynucleotide comprising SEQ ID NO: 2 which, when transduced into a human liver cell expresses the arginase 1 protein (SEQ ID NO: 1). Illustrative working embodiments of this are shown in FIGS. 1 and 2.

In other embodiments, the composition comprises an adeno-associated viral vector encoding the polynucleotide comprising SEQ ID NO: 4 which, which, when transduced into a human liver cell expresses the arginase 2 protein (SEQ ID NO: 3). Optionally in these compositions the adeno-associated viral vector comprises a polynucleotide comprising a terminal repeat sequence of SEQ ID NO: 5, a polynucleotide comprising a terminal repeat sequence of SEQ ID NO: 9, a polynucleotide comprising a chimeric intron sequence of SEQ ID NO: 7, a polynucleotide comprising a promoter sequence of SEQ ID NO: 6, and/or a polynucleotide comprising a polyA tail sequence of SEQ ID NO: 8.

Other embodiments of the invention include methods of delivering an arginase 1 polynucleotide or an arginase 2 polynucleotide into human cells, the methods comprising contacting an adeno-associated viral vector comprising SEQ ID NO: 2 or an adeno-associated viral vector comprising SEQ ID NO: 4 with the human cells so that adeno associated vector(s) infect the human cells, thereby delivering the polynucleotides into the human cells. In illustrative embodiments, the human cells are in vivo liver cells, for example, those present in an individual diagnosed with an arginase 1 or 2 deficiency. In some embodiments, the adeno associated viral vector comprises the polynucleotide comprising SEQ ID NO: 2 which, when transduced into the human liver cell expresses the arginase 1 protein (SEQ ID NO: 1). Illustrative working embodiments of this are shown in FIG. 2, In other embodiments, the adeno associated viral vector comprises the polynucleotide comprising SEQ ID NO: 4 which, which, when transduced into the human liver cell expresses the arginase 2 protein (SEQ ID NO: 3). In certain embodiments of the invention, the adeno associated viral vector is delivered intravenously.

Other embodiments of the invention include kits such as a kit comprising a composition that includes a polynucleotide comprising SEQ ID NO: 2 or a polynucleotide comprising SEQ ID NO: 4 disposed in one or more containers. In certain embodiments of the invention, the kit comprises an adeno-associated viral vector comprising a polynucleotide sequence having a constellation of elements designed to facilitate arginase 1 protein or arginase 2 protein expression in human cells, for example a sequence comprising a terminal repeat sequence, a polynucleotide sequence comprising a liver specific promoter, a polynucleotide comprising SEQ ID NO: 2 or a polynucleotide comprising SEQ ID NO: 4, a polynucleotide sequence comprising a polyA tail signal. The one or more containers can further comprise a pharmaceutical excipient selected from the group consisting of a preservative, a tonicity adjusting agent, a detergent, a viscosity adjusting agent, a sugar or a pH adjusting agent. Optionally, the adeno-associated viral vector comprises a polynucleotide comprising a terminal repeat sequence of SEQ ID NO: 5, a polynucleotide comprising a terminal repeat sequence of SEQ ID NO: 9, a polynucleotide comprising a chimeric intron sequence of SEQ ID NO: 7, a polynucleotide comprising a promoter sequence of SEQ ID NO: 6, and/or a polynucleotide comprising a polyA tail sequence of SEQ ID NO: 8. In certain kit embodiments, the composition comprises an adeno-associated viral vector encoding the polynucleotide comprising SEQ ID NO: 2 which, when transduced into a human liver cell expresses the arginase 1 protein (SEQ ID NO: 1). In other kit embodiments, the composition comprises an adeno-associated viral vector encoding the polynucleotide comprising SEQ ID NO: 4 which, which, when transduced into a human liver cell expresses the arginase 2 protein (SEQ ID NO: 3). Additional aspects of the invention are discussed below.

Compositions comprising AAV constructs (e.g. the AAV constructs disclosed herein) of the invention can be formulated as pharmaceutical compositions in a variety of forms adapted to the chosen route of administration. The compounds of the invention are typically administered in combination with a pharmaceutically acceptable vehicle such as an inert diluent. For compositions suitable for administration to humans, the term "excipient" is meant to include, but is not limited to, those ingredients described in Remington: The Science and Practice of Pharmacy, Lippincott Williams & Wilkins, 21st ed. (2006) the contents of which are incorporated by reference herein.

The compounds may also be administered in a variety of ways, for example intravenously. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

Useful liquid carriers include water, alcohols or glycols or water/alcohol/glycol blends, in which the compounds can be dissolved or dispersed at effective levels, optionally with the aid of non-toxic surfactants. Adjuvants such as additional antimicrobial agents can be added to optimize the properties for a given use.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See e.g., The Pharmacological Basis of Therapeutics, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and Whether the treatment is prophylactic). Treatment may involve daily or multi-daily doses of compound(s) over a period of a few days to months.

In certain embodiments of the invention, AAV constructs disclosed herein may be used for the preparation of a pharmaceutical composition for the treatment of disease. Such disease may comprise a disease treatable by gene therapy, including arginase 1 and arginase 2 deficiency. The term "pharmaceutical composition", as used herein, refers to a composition comprising a therapeutically effective amount of active agents of the present invention and at least one non-naturally occurring pharmaceutically acceptable excipient. Embodiments of the invention relate to pharmaceutical compositions comprising one or more AAV constructs disclosed herein in combination with a pharmaceutically acceptable excipient.

The terms "pharmaceutically acceptable excipient", or "pharmaceutically acceptable carrier," "pharmaceutically acceptable diluent,", or "pharmaceutically acceptable vehicle," used interchangeably herein, refer to a non-toxic solid, semisolid or liquid filler, diluent, encapsulating material or formulation auxiliary of any conventional type. A pharmaceutically acceptable carrier is essentially non-toxic to recipients at the dosages and concentrations employed and is compatible with other ingredients of the formulation. Suitable carriers include, but are not limited to water, dextrose, glycerol, saline, ethanol, and combinations thereof. The carrier can contain additional agents such as wetting or emulsifying agents, pH buffering agents, or adjuvants which enhance the effectiveness of the formulation.

The person skilled in the art will appreciate that the nature of the excipient in the pharmaceutical composition of the invention will depend to a great extent on the administration route. In the case of the pharmaceutical compositions formulated for use in gene therapy regimens, a pharmaceutical composition according to the invention normally contains the pharmaceutical composition of the invention mixed with one or more pharmaceutically acceptable excipients. These excipients can be, for example, inert fillers or diluents, such as sucrose, sorbitol, sugar, mannitol, microcrystalline cellulose, starches, including potato starch, calcium carbonate, sodium chloride, lactose, calcium phosphate, calcium sulfate or sodium phosphate; crumbling agents and disintegrants, for example cellulose derivatives, including microcrystalline cellulose, starches, including potato starch, sodium croscarmellose, alginates or alginic acid and chitosans; binding agents, for example sucrose, glucose, sorbitol, acacia, alginic acid, sodium alginate, gelatin, starch, pregelatinized starch, microcrystalline cellulose, aluminum magnesium silicate, sodium carboxymethylcellulose, methylcellulose, hydroxypropyl methylcellulose, ethylcellulose, polyvinylpyrrolidone, polyvinyl acetate or polyethylene glycol, and chitosans; lubricating agents, including glidants and antiadhesive agents, for example magnesium stearate, zinc stearate, stearic acid, silicas, hydrogenated vegetable oils or talc.

The present invention further provides methods associated with gene therapy regimens such as methods of delivering a nucleic acid encoding a codon optimized arginase 1 or arginase 2 sequence into a cell so that the cell expresses arginase 1 or arginase 2 protein. In such methods, the virus may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of an AAV vector(s) of the present invention (e.g. the AAV constructs disclosed herein) can be accomplished by any other means known in the art.

Recombinant AAV virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell. The cell to be administered the inventive virus vector may be of any type, including but not limited to hepatic cells.

A "therapeutically-effective" amount as used herein is an amount that is sufficient to alleviate (e.g., mitigate, decrease, reduce) at least one of the symptoms associated with a disease state (e.g. one caused by arginase 1 deficiency) Alternatively stated, a "therapeutically-effective" amount is an amount that is sufficient to provide some improvement in the condition of the subject. Data from an illustrative working embodiments of this is shown in FIG. 2.

A further aspect of the invention is a method of treating subjects in vivo with the inventive viral constructs. Administration of the AAV constructs of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formulation.

In particularly preformed embodiments of the invention, the nucleotide sequence(s) of interest is/are delivered to the liver of the subject. Administration to the liver may be achieved by any method known in art, including, but not limited to intravenous administration, intraportal administration, intrabilary administration, intra-arterial administration, and direct injection into the liver parenchyma.

The following table shows the polypeptide and polynucleotide sequences useful in embodiments of the invention.

TABLE 1

POLYNUCLEOTIDE AND POLYPEPTIDE SEQUENCES
Embodiments of the invention include adeno-
associated viral vectors selected to have a
number of elements that facilitate arginase
1 or arginase 2 protein expression in human
cells (e.g. liver cells) such as terminal
repeat sequences (e.g. ITRs). introns,
promoters (e.g a liver specific promoters),
codon optimized sequences. poly A signal
sequences and the like. Illustrative but
nonlimiting sequences from the working
embodiments of the intention disclosed
herein are protided below.

ARG1: arginase 1 Protein
ACCESSION P05089
REFERENCE:
Haraguchi et al., Proc. Natl. Acad. Sci.
U.S.A. 84 (2), 412-415 (1987).
MSAKSRTIGIIGAPFSKGQPRGGVEEGPTVLRKAG
LLEKLKEQECDVKDYGDLPFADIPNDSPFQIVKNP
RSVGKASEQLAGKVAEVKKNGRISLVLGGDHSLAI
GSISGHARVHPDLGVIWVDAHTDINTPLTTTSGNL
HGQPVSFLLKELKGKIPDVPGFSWVTPCISAKDIV
YIGLRDVDPGEHYILKTLGIKYFSMTEVDRLGIGK
VMEETLSYLLGRKKRPIHLSFDVDGLDPSFTPATG
TPVVGGLTYRSGLYITEEIYKTGLLSGLDIMEVNP
SLGKTPEEVTRTVNTAVAITLACFGLAREGNHKPI
DYLNPPK
(SEQ ID NO: 1)

ARG2: arginase 2 Protein
NCBI Reference Sequence: NP_001163.1
REFERENCE: McGovern et. al., Nature 546
(7660), 662-666 (2017)
MSLRGSLSRLLQTRVHSILKKSVESVAVIGAPFSQ
GQKRKGVEHGPAAIREAGLMKRLSSLGCHLKDFGD
LSFTPVPKDDLYNNLIVNPRSVGLANQELAEVVSR
AVSDGYSCVTLGGDKSLAIGTISGHARHCPDLCVV
WVDAEADINTPLTTSSGNLHGQPVSFLLRELQDKV
PQLPGFSWIKPCISSASIVYIGLRDVDPPEHFILK TABLE 1-continued POLYNUCLEOTIDE AND POLYPEPTIDE SEQUENCES
Embodiments of the invention include adeno-
associated viral vectors selected to have a
number of elements that facilitate arginase
1 or arginase 2 protein expression in human
cells (e.g. liver cells) such as terminal
repeat sequences (e.g. ITRs). introns,
promoters (e.g a liver specific promoters),
codon optimized sequences. poly A signal
sequences and the like. Illustrative but
nonlimiting sequences from the working
embodiments of the intention disclosed
herein are protided below.

NYDIQYFSMRDIDRLGIQKVMERTFDLLIGKRQRP
IKLSFDIDAFDPTLAPATGTPVVGGLTYREGMYIA
EEIHNTGLLSALDLVEVNPQLATSEEEAKTTANLA
VDVIASSFGQTREGGHIVYDQLPTPSSPDESENQA
RVRI
(SEQ ID NO: 3)

Full-length sequence of the codon
optimized human ARG1 sequence
Full-leneth hcoARG1:
ATGAGCGCAAAGTCTCGAACAATTGGCATAATTGG
TGCTCCGTTCAGCAAAGGTCAGCCAAGGGGCGGCG
TGGAGGAAGGACCCACAGTGCTGAGAAAAGCCGGC
CTGCTGGAGAAACTGAAGGAACAGGAATGTGACGT
GAAGGACTATGGGGATCTGCCTTTTGCCGATATAC
CGAATGATTCACCCTTCCAAATTGTGAAAAATCCA
AGATCCGTGGGCAAAGCAAGTGAACAGTTGGCCGG
GAAGGTGGCAGAGGTTAAAAAAAATGGAAGGATCA
GCCTCGTACTGGGTGGCGATCACTCTCTTGCAATT
GGAAGTATTTCAGGCCATGCCCGCGTTCATCCCGA
TCTCGGCGTGATCTGGGTTGATGCTCATACAGATA
TCAATACCCCTCTGACGACAACATCTGGGAACCTG
CATGGACAACCTGTATCATTTCTGTTGAAGGAACT
GAAAGGCAAAATACCCGACGTGCCTGGATTTTCAT
GGGTGACCCCCTGCATCTCTGCTAAAGACATAGTT
TACATAGGTCTGCGCGACGTTGATCCTGGAGAACA
TTACATTCTCAAGACACTCGGAATTAAATATTTCA
GTATGACAGAAGTGGACCGCCTCGGGATTGGCAAA
GTAATGGAGGAGACTCTTTCATACCTGCTGGGACG
CAAAAAACGACCGATTCACCTCAGCTTTGACGTCG
ATGGACTTGACCCATCTTTTACACCAGCTACTGGA
ACACCAGTTGTAGGAGGTCTTACTTACCGCGAAGG
TCTGTATATAACTGAAGAGATTTATAAGACTGGAC
TTCTCAGTGGACTTGATATTATGGAAGTGAACCCT
AGCCTGGGAAAAACACCAGAAGAAGTCACACGCAC
CGTCAATACCGCCGTGGCTATCACCCTGGCTTGTT
TCGGCTTGGCACGCGAAGGGAATCATAAACCTATT
GACTACCTGAATCCCCCAAAGTAA
(SEQ ID NO: 2)

Full-length sequence of the codon-
optimized human ARG2 sequence
Full-length hcoARG2:
ATGGTCCACAGCGTTGCCGTCATTGGTGCACCATT
CTCACAAGGCCAGAAAAGAAAGGGCGTGGAACATG
GCCCTGCTGCAATAAGAGAGGCCGGACTGATGAAA
AGACTGTCTTCCCTTGGCTGCCATCTTAAAGACTT
CGGTGATCTCAGCTTCACTCCTGTTCCGAAAGACG
ACCTCTACAACAACCTTATCGTAAATCCTAGATCC
GTAGGTCTTGCTAATCAAGAATTGGCTGAGGTGGT
TTCCCGAGCAGTTTCCGACGGATATAGCTGCGTGA
CCCTCGGCGGTGACCATTCGCTGGCAATTGGTACA
ATTAGCGGACACGCAAGACATTGCCCTGATCTCTG
TGTGGTATGGGTTGACGCGCATGCTGATATAAATA
CGCCTCTCACCACCTCCTCTGGCAATCTGCACGGA
CAGCCCGTGTCCTTTCTCCTCCGCGAACTCCAGGA
CAAGGTGCCACAACTCCCCGGGTTCTCTTGGATCA
AGCCCTGCATTTCATCCGCTAGTATAGTGTACATC
GGCCTTAGAGACGTCGACCCACCAGAGCATTTCAT
CCTCAAAAATTATGACATTCAGTACTTTAGTATGC
GCGACATTGACAGGCTGGGTATTCAGAAAGTGATG
GAAAGGACGTTCGACCTGTTGATCGGCAAAAGACA
GAGACCAATTCACCTCAGCTTTGATATTGATGCAT
TCGATCCTACGCTCGCTCCGGCAACAGGGACACCA
GTGGTAGGAGGCCTGACTTATAGAGAAGGTATGTA
CATAGCCGAAGAAATACACAACACTGGACTGCTTA

TABLE 1-continued

POLYNUCLEOTIDE AND POLYPEPTIDE SEQUENCES

Embodiments of the invention include adeno-associated viral vectors selected to have a number of elements that facilitate arginase 1 or arginase 2 protein expression in human cells (e.g. liver cells) such as terminal repeat sequences (e.g. ITRs). introns, promoters (e.g a liver specific promoters), codon optimized sequences. poly A signal sequences and the like. Illustrative but nonlimiting sequences from the working embodiments of the intention disclosed herein are protided below.

```
GCGCGCTTGACCTTGTTGAAGTTAATCCCCAGCTC
GCCACGTCCGAGGAAGAGGCCAAGACCACAGCTAA
TCTCGCAGTTGATGTAATAGCATCTAGTTTTGGAC
AGACCCGAGAAGGAGGGCACATCGTGTATGACCAG
CTCCCTACACCGAGTTCACCTGATGAGTCAGAAAA
TCAAGCCCGGGTCCGCATTTAG
(SEQ ID NO. 4)
```

Illustrative 5' ITR sequence
```
CTGCGCGCTCGCTCGCTCACTGAGGCCGCCCGGGC
AAAGCCCGGGCGTCGGGCGACCTTTGGTCGCCCGG
CCTCAGTGAGCGAGCGAGCGCGCAGAGAGGGAGTG
GCCAACTCCATCACTAGGGGTTCCt
(SEQ ID NO. 5)
```

Illustrative promoter sequence
Thyroxine Biriding Globulin (TBG) promoter
```
GGGCTGGAAGCTACCTTTGACATCATTTCCTCTGC
GAATGCATGTATAATTTCTACAGAACCTATTAGAA
AGGATCACCCAGCCTCTGCTTTTGTACAACTTTCC
CTTAAAAAACTGCCAATTCCACTGCTGTTTGGCCC
AATAGTGAGAACTTTTTCCTGCTGCCTCTTGGTGC
TTTTGCCTATGGCCCCTATTCTGCCTGCTGAAGAC
ACTCTTGCCAGCATGGACTTAAACCCCTCCAGCTC
TGACAATCCTCTTTCTCTTTTGTTTTACATGAAGG
GTCTGGCAGCCAAAGCAATCACTCAAAGTTCAAAC
CTTATCATTTTTTGCTTTGTTCCTCTTGGCCTTGG
TTTTGTACATCAGCTTTGAAAATACCATCCCAGGG
TTAATGCTGGGGTTAATTTATAACTAAGAGTGCTC
TAGTTTTGCAATACAGGACATGCTATAAAAATGGA
AAGAT
(SEQ ID NO. 6)
```

Illustrative Chimeric Intron sequence
```
GTAAGTATCAAGGTTACAAGACAGGTTTAAGGAGA
CCAATAGAAACTGGGCTTGTCGAGACAGAGAAGAC
TCTTGCGTTTCTGATAGGCACCTATTGGTCTTACT
GACATCCACTTTGCCTTTCTCTCCACAG
(SEQ ID NO. 7)
```

Illustrative polyA signal sequence
```
GATCTTTTTCCCTCTGCCAAAAATTATGGGGACAT
CATGAAGCCCCTTGAGCATCTGACTTCTGGCTAAT
AAAGGAAATTTATTTTCATTGCAATAGTGTGTTGG
AATTTTTTGTGTCTCTCACTCG
(SEQ ID NO. 8)
```

Illustrative 3' 1TR sequence
```
AGGAACCCCTAGTGATGGAGTTGGCCACTCCCTCT
CTGCGCGCTCGCTCGCTCACTGAGGCCGGGCGACC
AAAGGTCGCCCGACGCCCGGGCTTTGCCCGGGCGG
CCTCAGTGAGCGAGCGAGCGCGCAG
(SEQ ID NO. 9)
```

CONCLUSION

This concludes the description of embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A method of making a pharmaceutical composition comprising combining together in an aqueous formulation:
   a polynucleotide comprising SEQ ID NO: 2 or a polynucleotide comprising SEQ ID NO: 4; and
   a pharmaceutical excipient selected from the group consisting of:
   a preservative, a tonicity adjusting agent, a detergent, a viscosity adjusting agent, a sugar or a pH adjusting agent.

2. The method of claim 1, wherein:
   the polynucleotide comprising SEQ ID NO: 2 or the polynucleotide comprising SEQ ID NO: 4 is disposed in an adeno-associated viral vector such that when the adeno-associated viral vector infects a human liver cell, arginase 1 protein encoded by the amino acid sequence of SEQ ID NO: 1 or arginase 2 protein encoded by the amino acid sequence of SEQ ID NO: 3 is expressed.

3. The method of claim 2, wherein the adeno-associated viral vector comprises:
a polynucleotide comprising a terminal repeat sequence of SEQ ID NO: 5;
a polynucleotide comprising a promoter sequence of SEQ ID NO: 6; and
a polynucleotide comprising a polyA tail sequence of SEQ ID NO: 8.

4. The method of claim 3, wherein the adeno-associated viral vector comprises a polynucleotide comprising SEQ ID NO: 2.

5. A composition of matter comprising:
a polynucleotide comprising SEQ ID NO: 2; or
a polynucleotide comprising SEQ ID NO: 4.

6. The composition of claim 5, wherein the composition comprises:
an adeno-associated viral vector comprising:
a polynucleotide sequence comprising a terminal repeat sequence;
a polynucleotide sequence comprising a liver specific promoter;
the polynucleotide comprising SEQ ID NO: 2 or the polynucleotide comprising SEQ ID NO: 4; and
a polynucleotide sequence comprising a polyA tail signal; and
a pharmaceutical excipient selected from the group consisting of:
a preservative, a tonicity adjusting agent, a detergent, a viscosity adjusting agent, a sugar or a pH adjusting agent.

7. The composition of claim 6, wherein the composition comprises the adeno-associated viral vector encoding the polynucleotide comprising SEQ ID NO: 2 which, when transduced into a human liver cell expresses the arginase 1 protein encoded by the amino acid sequence of SEQ ID NO: 1.

8. The composition of claim 6, wherein the composition comprises the adeno-associated viral vector encoding the polynucleotide comprising SEQ ID NO: 4 which, which, when transduced into a human liver cell expresses the arginase 2 protein encoded by the amino acid sequence of SEQ ID NO: 3.

9. The composition of claim 7 or claim 8, wherein the adeno-associated viral vector comprises:
the polynucleotide sequence comprising the terminal repeat sequence of SEQ ID NO: 5;
the polynucleotide sequence comprising the terminal repeat sequence of SEQ ID NO: 9;
a polynucleotide sequence comprising a chimeric intron sequence of SEQ ID NO: 7;
the polynucleotide sequence comprising the liver specific promoter of SEQ ID NO: 6; or
the polynucleotide sequence comprising the polyA tail signal of SEQ ID NO: 8.

10. A method of delivering an arginase 1 polynucleotide or an arginase 2 polynucleotide into human cells, the method comprising:
contacting a composition of claim 6 with the human cells so that the adeno-associated vector infects the human cells, thereby delivering the polynucleotides into the human cells.

11. The method of claim 10, wherein the human cells are in vivo liver cells.

12. The method of claim 10, wherein the in vivo liver cells are present in an individual diagnosed with an arginase 1 or arginase 2 deficiency.

13. The method of claim 12, wherein the adeno-associated viral vector comprises the polynucleotide comprising SEQ ID NO: 2 which, when transduced into the human liver cell expresses the arginase 1 protein encoded by the amino acid sequence of SEQ ID NO: 1.

14. The method of claim 12, wherein the adeno-associated viral vector comprises the polynucleotide comprising SEQ ID NO: 4 which, when transduced into the human liver cell expresses the arginase 2 protein encoded by the amino acid sequence of SEQ ID NO: 3.

15. The method of claim 12, wherein the adeno-associated viral vector is delivered intravenously.

16. A kit comprising:
a polynucleotide comprising SEQ ID NO: 2 or a polynucleotide comprising SEQ ID NO: 4 disposed in one or more containers.

17. The kit of claim 16, wherein the kit comprises:
an adeno-associated viral vector comprising:
a polynucleotide sequence comprising a terminal repeat sequence;
a polynucleotide sequence comprising a liver specific promoter;
the polynucleotide comprising SEQ ID NO: 2 or the polynucleotide comprising SEQ ID NO: 4; and
a polynucleotide sequence comprising a polyA tail signal; and
a pharmaceutical excipient selected from the group consisting of:
a preservative, a tonicity adjusting agent, a detergent, a viscosity adjusting agent, a sugar or a pH adjusting agent.

18. The kit of claim 17, wherein the composition comprises the adeno-associated viral vector encoding the polynucleotide comprising SEQ ID NO: 2 which, when transduced into a human liver cell expresses an arginase 1 protein encoded by the amino acid sequence of SEQ ID NO: 1.

19. The kit of claim 17, wherein the composition comprises the adeno-associated viral vector encoding the polynucleotide comprising SEQ ID NO: 4 which, when transduced into a human liver cell expresses an arginase 2 protein encoded by the amino acid sequence of SEQ ID NO: 3.

20. The kit of claim 18 or claim 19, wherein the adeno-associated viral vector comprises:
the polynucleotide sequence comprising the terminal repeat sequence of SEQ ID NO: 5;
the polynucleotide sequence comprising the terminal repeat sequence of SEQ ID NO: 9;
a polynucleotide sequence comprising a chimeric intron sequence of SEQ ID NO: 7;
the polynucleotide sequence comprising the liver specific promoter of SEQ ID NO: 6; or
the polynucleotide comprising the polyA tail signal of SEQ ID NO: 8.

* * * * *